(12) United States Patent
Rapaport

(10) Patent No.: US 6,723,737 B1
(45) Date of Patent: Apr. 20, 2004

(54) METHODS, PHARMACEUTICAL AND THERAPEUTIC COMPOSTIONS FOR ADMINISTERING ADENOSINE

(76) Inventor: Eliezer Rapaport, 14 Prentiss La., Belmont, MA (US) 02178

( * ) Notice: Subject to any disclaimer, the term of this patent is extended or adjusted under 35 U.S.C. 154(b) by 5 days.

(21) Appl. No.: 10/111,167

(22) PCT Filed: Oct. 18, 2000

(86) PCT No.: PCT/US00/28769

§ 371 (c)(1),
(2), (4) Date: Apr. 22, 2002

(87) PCT Pub. No.: WO01/28528

PCT Pub. Date: Apr. 26, 2001

Related U.S. Application Data

(60) Provisional application No. 60/160,634, filed on Oct. 20, 1999.

(51) Int. Cl.$^7$ .................. A61K 31/7076; A61K 31/52; C12P 19/32; C07M 19/20; C07M 19/04

(52) U.S. Cl. .................. 514/310; 514/43; 514/45; 514/46; 514/58; 514/54; 514/60; 514/909; 424/464; 424/468; 424/474; 424/479; 424/480; 424/475; 536/26.26

(58) Field of Search .................. 514/310, 43, 45, 514/46, 58, 54, 60, 909; 424/464, 468, 474, 479, 480, 475; 536/26.26

(56) References Cited

U.S. PATENT DOCUMENTS 5,017,564 A  *  5/1991  Makino et al. ............. 514/47

OTHER PUBLICATIONS

Voet et al., Fundamentals of Biochemistry, John Wiley & Sons, Inc., 1999, p. 44.*
Remington's Pharmaceutical Sciences, Fifteenth Edition, 1975, pp. 1587 and 1614–1615.*
Paul J. Arciero et al., AGE and NE and FFA Kinetics After Caffeine Ingestion, pp. E1192–E1198, Effects of Caffeine Ingestion on NE Kinetics, Fat Oxidation, and Energy Expenditure in Younger and Older Men.
G. Burnstock, Part 1. Biological Effects of Extracellular ATP and Nucleotides, pp. 1–17, Purinergic Mechanisms.
Council on Scientific Affairs, Council Report, JAMA, 1988, vol. 260, No. 17, pp. 2547–2551, Treatment of Obesity in Adults.
Hoppe et al., 16. Desensitization of A1 Adenosine Receptors, pp. 133–138.
Kenneth A. Jacobson et al., Purinergic Approaches in Experimental Therapeutics,, 1997, pp. 102–129, Development of Selective Purinoceptor Agonists and Antagonists.
Kollias–Baker et al., 26. Myocardial Adenosine Receptors, pp. 221–228.
Kathryn La Noue et al., The FASEB Journal, 1994, vol. 8, pp. 72–80, Abnormal A1 Adenosine Receptor Function in Genetic Obesity.
H. Thomas Lee et al., The American Physiological Society, 1993, pp. H1916–H1927, Cardiac Desensitization to Adenosine Analogues After Prolonged R–PIA Infusion in Vivo.
Joel Linden, The FASEB Journal, 1991, vol. 5 pp. 2668–2676, Structure and Function A1 Adenosine Receptors.
Joel Linden, Purinergic Approaches in Experimental Therapeutics, 1997, pp. 84–97, Allosteric Enhancement of Adenostine Receptors.
Khalid A. Mohamedali et al., The Journal of Biological Chemistry, 1993, vol. 268., No. 31, pp. 23728–23733, The Highest Levels of Purine Catabolic Enzymes in Mice are Present in the Proximal Small Intestine.
Eliezer Rapaport, Department of Microbiology, pp. 142–149, Mechanisms of Anticancer Activities of Adenine Nucleotides in Tumor–Bearing Hosts.
Eliezer Rapaport et al., Proc. Natl. Acad Sci. USA, 1976, vol. 73, No. 9, pp. 3122–3125, Incorporation of Adenosine Into ATP:Formation of Compartmentalized ATP.
Eliezer Rapaport et al., Biochemical Pharmacology, 1989, vol. 38 No. 23 pp. 4261–4266, Generation of Extracellular ATP in Blood and its Mediated Inhibition of Host Weight Loss in Tumor–Bearing Mice.
Eliezer Rapaport et al. Proc. Natl. Acad. Sci., 1989, vol. 86, pp. 1662–1666, Anticancer Activities of Adenine Nucleotides in Mice Are Mediated Through Expansion of Erythrocyte ATP Pools.
John Shryock et al., The American Physiological Society, 1989, pp. H321–H327, Downregulation And Desensitization of A1–Adenosine Receptors in Embryonic Chicken Heart.
Linda L. Slakey et al., Part V. Metabolism and Utilization of Extracellular ATP by Ectoenzymes, pp. 366–379, A Comparsion of Ectonucleotidase Activities On Vascular Endothelial and Smooth Muscle Cells$^a$.

(List continued on next page.)

Primary Examiner—Frederick Krass
Assistant Examiner—Clinton Ostrup
(74) Attorney, Agent, or Firm—Connolly Bove Lodge & Hutz, LLP

(57) ABSTRACT

The invention discloses methods for the chronic administration of adenosine, which contrary to the acute delivery of the drug by injection or infusion, acts in desensitizing adenosine receptors towards the action of adenosine. The methods and oral compositions of adenosine triphosphate (ATP), which is degraded to adenosine in vivo, can be used in the treatment of disorders and diseases that are therapeutically targeted by agonists or antagonists of adenosine receptors. One example is the stimulation of lipolysis in achieving weight loss in humans and in the treatment of obesity.

27 Claims, No Drawings

OTHER PUBLICATIONS

P.H. Van Der Graff et al., The Journal of Pharmacology and Experimental Therapeutics, 1999, vol. 290, No.2, pp. 702–709, Mechanism–Based Pharmacokinetic–Pharmacodynamic Modeling of Antilipolytic Effects of Adenosine A1 Receptor Agonists in Rats: Prediction of Tissue–Dependent Efficacy in Vivo.

E.A. Van Schaick et al., The Journal Of Pharmacology and Experimental Therapeutics, 1998, vol. 287, No. 1, pp. 21–30, Metabolic And Cardiovascular Effects of The Adenosine A1 Receptor Agonis N6–(p–Sulfophenyl) Adenosine in Diabetic Zucker Rats: Influence of the Disease on the Selectivity of Action.

Michael Williams et al., Purinergic Approaches in Experimental Therapeutics, 1997, pp. 3–26, Purinergic Neurotransmission and Neuromodulation a Historical Perspective.

Baiyand Xu et al., The American Physiological Society, 1998, pp. E271–E279, A1 Adenosine Receptor Antagonism Improves Glucose Tolerance in Zucker Rats.

* cited by examiner-

METHODS, PHARMACEUTICAL AND THERAPEUTIC COMPOSTIONS FOR ADMINISTERING ADENOSINE

This application claims the benefit of provisional application No. 60/160,634, filed Oct. 20, 1999.

FIELD OF THE INVENTION

The invention relates to the chronic elevation of endogenous adenosine levels by the use of stable adenosine 5'-triphosphate (ATP) compositions, which are taken orally over a period of time. The elevated levels of adenosine, produced by the in vivo degradation of ATP, act in decreasing the sensitivity (desensitization) of adenosine receptors. The decrease in sensitivity can materialize through a decrease in numbers of receptors (density) or through a reduction in the receptor's coupling activity (intracellular signal transduction). The reduced sensitivity of certain adenosine receptors towards their natural agonist—adenosine, can be useful by itself or in combination with adenosine antagonists, which are much more active towards desensitized adenosine receptors. Examples for utilization of these methods are in the treatment of disorders or diseases, which are controlled by biochemical mechanisms regulated by adenosine receptors. One such case is in the treatment of obesity, which can be treated by the metabolic stimulation of weight loss. Lipolysis, the degradation of fat (triglycerides) in adipose tissue to free fatty acids and glycerol, is known to be inhibited by the interaction of adenosine with $A_1$ adenosine receptors of the adipocyte (fat cell). The interaction of adenosine with adipose tissue $A_1$ adenosine receptors was shown to stimulate lipogenesis—the buildup of triglycerides (fat) in fat cells. Methods for desensitization of $A_1$ adenosine receptors in a human in vivo, thus significantly diminishing the activity of endogenous adenosine, are disclosed and taught and are utilized for the effective reduction of weight in humans. Effective weigh loss in humans can be achieved either by the desensitization of the adipose tissue adenosine $A_1$ receptors by themselves, or by desensitization in combination with adenosine antagonists such as caffeine or theophylline, which are much more effective in blocking the action of adenosine once its receptors became desensitized. The use of chronic administration of adenosine for the purpose of desensitization of adipose tissue $A_1$ adenosine receptors in the induction of weight loss in humans, demonstrates the utility of the present invention. Obesity is the costliest disease in industrialized countries. It is associated with a variety of chronic life-threatening diseases such as type II diabetes, hypertension, stroke, and heart disease. The definition of obesity is an excessive accumulation of fat in the body. Obesity in terms of a disease is defined if body weight is 20% or more above the desirable weight (Council on Scientific Affairs, J. Amer. Med. Assoc. 1988). Overweight is defined if body weight exceeds the desirable weight by less than 20%. Desirable weight in humans has been well-defined (council on scientific affairs, JAMA 1988). Weight loss in overweight or obese humans can be achieved by diet, physical activity and behavior modification or by treatment with drugs. There are three main ways for the pharmaceutical treatment of overweight or obesity: 1. Inhibition of absorption of nutrients in the intestine; 2. Modulation of the activities of the metabolic and central nervous system (hypothalamic) satiety and food consumption (hunger) signals; and 3. Induction of energy dissipation in tissues, especially adipose tissue (thermogenesis). The methods disclosed here of the chronic administration of adenosine by the oral delivery of the pro-drug ATP, deal with the induction of energy dissipation, in the form of degradation of fats in adipose tissue.

BACKGROUND OF INVENTION

The physiological activities of adenosine triphosphate and adenosine were first discovered in 1929 (for a review, see Williams and Bumstock 1997). It is now known that adenosine exerts its physiological effects by interacting with specific receptors, several subtypes of which ($A_1$, $A_{2A}$, $A_{2B}$ and $A_3$) have been characterized and shown to regulate specific physiological processes. Adenosine triphosphate in turn, exerts its physiological activities by interacting with another family of receptors termed $P_2$ receptors (Bumstock 1990). The $A_1$ adenosine receptors were shown to regulate significant brain (Williams and Bumstock 1997); heart and adipose tissue functions (van der Graaf et al. 1999) by their in vivo interactions with endogenous, extracellular adenosine in animals and humans. The function of these $A_1$ adenosine receptors is to transmit regulatory signals from adenosine, which is the product of extracellular metabolism, to the inside of the cells. This signal transduction is in turn achieved by a family of G proteins-linked to cell membrane $A_1$ adenosine receptors (Linden 1991). The $G_i$ protein, which interacts with the $A_1$ adenosine receptors, acts in inhibiting the intracellular activity of adenyl cyclase, the enzyme catalyzing the synthesis of cyclic AMP (cAMP) inside the cell. Thus, upon interaction of extracellular adenosine with $A_1$ adenosine receptors, the $G_i$ proteins coupled to this receptor inhibit the synthesis of cAMP, resulting in lower cellular levels of cAMP and in the case of adipose $A_1$ adenosine receptors, overall inhibition of lipolysis (LaNoue and Martin 1994). Because signaling from the adipose tissue $A_1$ adenosine receptors inhibit the degradation of triglycerides to free fatty acids and glycerol (lipolysis), the possibility of excessive activity of the adipose tissue $A_1$ adenosine receptors was considered as a genetic factor in obesity. This indeed turned out to be the case in genetically obese mice and rats as well as in humans. In these cases the adipose tissue $A_1$ adenosine receptors were found to be extremely active in transmitting their signal to the $G_i$ proteins with little dependence on the presence of extracellular adenosine (LaNoue and Martin 1994).

Therefore, the inhibition of the activity of adipose tissue $A_1$ adenosine receptors via antagonism of adenosine or a mediated reduction of the efficacy of the receptors'coupling to $G_i$ proteins would constitute a reasonable approach to weight control or obesity in humans. Methods utilizing the administration of $A_1$ adenosine receptor antagonists, such as caffeine (1,3,7-trimethylxanthine), theophylline (1,3-dimethylxanthine) or synthetic $A_1$ adenosine receptor antagonists, did not produce weight loss in genetically obese experimental animals (Xu et al. 1998). However, Caffeine, which is an established non-specific $A_1$ adenosine receptor antagonist (Jacobson and van Rhee 1997), was shown effective in inducing weight loss in humans as part of a variety of regimens discussed in several issued U.S. patents.

U.S. Pat. No. 5,422,352 discloses a combination of caffeine and ephedrine in a ratio of about 12:1 as a composition for reducing weight in humans. U.S. Pat. No. 5,480,657 discloses a composition of caffeine, chromium and fructose for the treatment of obesity. U.S. Pat. No. 5,679,358 discloses compositions containing caffeine, theophylline or their derivatives along with other ingredients for the purpose of reduction of superfluous fat of any origin by topical application. For example, this patent refers to caffeine, theophylline or pentoxifylline as lipolytic agents, though no mechanism is discussed in the specifications. U.S. Pat. No.

5,798,101 discloses compositions and methods for reducing weight consisting of St. John's Wart herbal extracts with or without caffeine. Caffeine and theophilline have been established as non-specific antagonists of adenosine receptors, namely, they interact with both $A_1$ and $A_{2A}$ adenosine receptors with moderate affinity (Jacobson and van Rhee 1997). All of the issued U.S. Patents discussed above refer to caffeine as a "stimulator of metabolism" or in one case a "lipolytic agent".

A published placebo-controlled double blind human clinical study has demonstrated that caffeine ingestion increased the levels of free fatty acids (the products of lipolysis) in young men in a statistically significant manner. The increase in free fatty acids after caffeine challenge was not related to alterations in norepinephrine kinetics or fat oxidation (Arciero et al. 1995).

Several physiological sites are regulated to a significant degree by $A_1$ adenosine receptors. These are the brain (Williams and Burnstock 1997), the heart (Kollias-Baker et al. 1995), adipose tissue (van der Graaf et al. 1999) and the coordination of glucose and lipid metabolism (van Schaick et al. 1998). Attempts to affect the function of specific organs or tissues by the use of adenosine or synthetic adenosine analogues acting as agonists or antagonists would seemingly produce global effects leading to intolerable side effects. This is not the case however, because of the blood brain barrier, which protects the brain from hydrophilic agents and the much greater sensitivity of adipocytes-metabolic $A_1$ adenosine receptors towards adenosine and its agonists in comparison to the heart $A_1$ adenosine receptors. The overall sensitivity of adipose tissue anti-lipolytic $A_1$ adenosine receptors towards adenosine, considering both the tissue density of the receptors and the sensitivity of the receptors' intracellular coupling, was reported to be 38 times higher than the sensitivity of $A_1$ adenosine receptors regulating cardiac functions (van der Graaf et al. 1999). Adipose tissue-metabolic $A_1$ adenosine receptors are therefore a good therapeutic target, taking into account their sensitivity towards adenosine in comparison to other potential therapeutic targets, which is expected to yield significant efficacy with a manageable spectrum of side effects. One condition is that the agonist for the adipose tissue-metabolic $A_1$ adenosine receptors has to be a relatively low affinity agonist, since a high affinity agonist is expected to interact with low affinity $A_1$ adenosine receptors on other organs and produce significant side effects (van der Graaf et al. 1999). Adenosine itself is known to be such an agonist (Jacobson and van Rhee 1997). The reason that it has not been used for these therapeutic targets is its extremely short blood plasma half-life, limiting any efficacy and potential usefulness (Williams and Burnstock 1997). The present invention discloses and teaches a method for consistently and chronically elevating blood plasma adenosine levels for achieving adipose tissue-metabolic therapeutic targets without any side-effects.

The short blood plasma half-life of adenosine of 3–6 seconds (Williams and Burnstock 1997) made it an ideal compound for the treatment of supraventricular tachycardia, a form of cardiac arrhythmia, for which use it has been approved in man as a bolus injection (Kollias-Baker et al. 1995). The therapeutic use of adenosine in the form of a bolus injection has been successful strictly because of the acute nature of the adenosine administration, preventing what is defined as receptor desensitization (Linden 1997). Chronic administration of synthetic $A_1$ adenosine receptor agonists was reported to produce marked desensitization of the heart's adenosine $A_1$ receptors (Shryock et al. 1989; Lee et al. 1993)

Desensitization of receptors is a general phenomenon, whereby chronic exposure of sensitive receptors to their agonists can produce a marked reduction in the capacity of the receptors to respond to the same or related agonists. The same phenomena have also been termed refractoriness, tolerance or tachyphylaxis (Hoppe and Lohse 1995). The $A_1$ adenosine receptors, both in cardiac and adipose tissues have been demonstrated to undergo desensitization after chronic exposure to adenosine analogues that are proven agonists for the $A_1$ adenosine receptors. Desensitization of the $A_1$ adenosine receptors in both tissues was demonstrated to be mediated by both a reduction in receptor density (numbers) and a decrease in the sensitivity of the receptor's coupling to the intracellular $G_i$ proteins (Hoppe and Lohse 1995). The $G_i$ proteins act in transducing the receptors' signal inside the target cell. The $A_1$ adenosine receptors desensitization is used as a therapeutic target as disclosed and taught by the present invention. By reducing the overall sensitivity of the adipose tissue-metabolic $A_1$ adenosine receptors as a result of chronic administration of adenosine, the effectiveness of adenosine as an endogenous anti-lipolytic agent is significantly diminished. As importantly, antagonism of adenosine at these sites, by common $A_1$ adenosine receptor antagonists such as caffeine or theophylline, is markedly enhanced. Desensitization of adipose tissue-metabolic $A_1$ adenosine receptors does not affect heart or brain $A_1$ adenosine receptors because of the heart's receptors much lower sensitivity (van der Graaf 1999) and the brain's effective barrier against systemic adenosine (Williams and Burnstock 1997).

SUMMARY OF THE INVENTION

The present invention discloses and teaches:

The preparation of a stable pharmaceutical and therapeutic composition of adenosine 5'-triphosphate (ATP) or physiologically acceptable salt thereof suitable for oral delivery. The invention provides for a stable oral dosage form such as a pill of ATP or physiologically acceptable salt thereof along with fillers, binders, stabilizers and enteric coating materials. The objective of the oral delivery of ATP is to achieve systemic absorption of adenosine.

A method for the chronic administration of adenosine using an ATP oral dosage form (e.g. pill) as a pro-drug for the chronic elevation of extracellular adenosine. Extracellular adenosine interacts with a variety of adenosine receptors regulating functions of organs and tissues.

A method for the chronic administration of adenosine for the purpose of desensitizing adipose tissue-metabolic $A_1$ adenosine receptors. The utility of this method is in decreasing the sensitivities of these receptors towards adenosine and at the same time increasing the sensitivities of these receptors towards adenosine antagonists such as caffeine or theophilline. This method is used for the purpose of inducing weight loss in humans or in the treatment of obesity in humans. Since the adipose tissue-metabolic A1 adenosine receptors act in inhibiting lipolysis (degradation of fats), reductions in their activities as a result of chronic exposure to adenosine is sufficient to induce lipolysis and effective weight loss. Chronic exposure to adenosine, can be supplemented by caffeine or theophilline, both commonly used drugs in order to further reduce the activities of adipose tissue-metabolic A1 adenosine receptors, thus achieving a more enhanced weight loss. The term "chronic administration" and similar terms used herein refer to prolonged or substantially sustained release over an extended period of time, typically at least about 96 hours.

DETAILED DESCRIPTION OF THE INVENTION

Pharmacologically active substances, such as ATP, which undergo rapid degradation inside parts of the gastrointestinal tract or inside the vascular bed, are coated with an enteric polymer that dissolves at a specific pH. In the case of ATP, the catabolic enzymes that catalyze the degradation of purines are present in the stomach and the proximal small intestines (Mohamedali et al. 1993). Thus a pH-sensitive enteric coating can be designed to release ATP as the therapeutically active agent in the distal part of the small intestine, the ileum, where catabolic activities that catalyze the degradation of ATP are minimal (Mohamedi et al. 1993). The human stomach has a variable acidic pH of about 1 to 2 and the transit time of a pill through the stomach is between 20 minutes and 2 hours, depending on the prandial state. An ATP pill passing through the stomach intact would enter the small intestine, which consists of the duodenum, jejunum and ileum. Transit time of a pill throughout the small intestine is relatively steady at approximately 3 hours. Following the small intestine, an enteric stable pill then passes through the large intestine, which consists of the caceum, the ascending colon, the transverse colon, the descending colon and the sigmoid colon. Total transit time through the large intestine is about 30–35 hours. Even though the distal part of the small intestine, the ileum, has somewhat greater catabolic activities on ATP than the colon, three of its properties make areas of the ileum very suitable sites for the release of ATP from enteric pills. First, a pH spectrum that enables the design of a pH-sensitive enteric coated pill, releasing the ATP at the desired site. The pH of the small intestine gradually rises from about 5–5.5 in the duodenal bulb, the site of gastric emptying, to about 7.2 in the distal parts of the ileum. The pH then drops at the ileum-caceum junction to about 6.3 and gradually increases to about 7 in the descending (left) colon. Second, absorption of purines from the small intestine is fast, providing for minimal degradation after release of the therapeutically active substance and a predictable delivery of specific dosage forms. Third, residence times to the point of release in the distal part of the small intestine are predictable (3–4.5 hours). Suitable tablets of adenosine 5'-triphosphate-disodium salt were prepared containing binders, fillers and stabilizers. The mixtures were granulated and condensed into 250 milligrams of ATP and 500 milligrams of ATP tablets using an oval-shaped punch. The tablets had to provide smooth surfaces, free from edges or sharp curves preferably with concave surfaces, all are properties desirable for the stability and mechanical strength of the enteric coating.

Stabilizers suitable for ATP disodium tablets are magnesium stearate, silica ($SiO_2$)(Sylox), which are suitable stabilizers in small well-established amounts, sodium bicarbonate, ascorbic acid, tocopherols, and maltodextrin, which is especially effective in protecting hygroscopic compositions such as ATP. Suitable fillers for use with ATP in a tablet include microcrystalline cellulose, carboxymethyl cellulose, mannitol or calcium phosphate-dibasic. Binders that are suitable for the ATP therapeutic composition include gum arabic, gelatin, polyvinylpyrrolidone (PVP), hydroxypropylcellulose (HPC) or methylcellulose. A preparation of ATP together with selected stabilizers, fillers and/or binders are then compressed into tablets of optimal size and shape to provide good mechanical strength and surface suitable for enteric coating. Instead of tablets, the blended preparations may be used to form capsules, microtablets or micropellets all of which may, or may not be enteric coated depending on the state of the art.

The function of the pH-dependent enteric coating is to prevent release of the therapeutically active pro-drug-ATP, until it reaches the targeted or desired location of the small intestine such as the distal portion of the small intestine, the section of the ileum where the pH rises to 7.2. The coating thickness is dependent upon the size and shape of the tablets and ranges from 20 to 80 .mu.m. Whereas the traditional enteric polymer coating materials were designed to protect the pharmaceutically active preparation in transit through the stomach, newer coating materials allow for the pH-dependent pills to dissolve only at higher pH's, with a great degree of accuracy. The older enteric polymer coating materials include cellulose acetate phthalate, polyvinylacetate phthalate, cellulose acetate trimelliate, polyvinyl acetate phthalate and hydroxypropyl methylcellulose phthalate. The preferred materials for enteric coating of ATP therapeutic compositions are methacrylic acid/methyl methacrylate copolymers, which are commercially available from Rhom Pharma under the name Eudragit S and Eudragit L. Eudragit S is a poly(metacrylic acid, methylmetacrylate) 1:2 and Eudragit L is a poly(metacrylic acid, methylmetacrylate) 1:1. Both are anionic copolymers where the ratios refer to the ratios of free carboxyl groups to methyl ester groups. Both copolymers have a mean molecular weight of 135,000. These two copolymers can be mixed in a variety of ratios to achieve a mechanically stable coating of pH sensitivity of between pH's 6 and 7, with Eudragit S being the preferred ingredient.

After the release of the therapeutic composition of ATP in the small intestine, absorption of adenosine and inorganic phosphate-the catabolic products of ATP, or of ATP itself then follows. Absorption of ATP itself is followed by a rapid degradation to adenosine and inorganic phosphate inside the vascular bed (Slakey et al. 1990; Rapaport and Fontaine 1989; Rapaport and Fontaine 1989b). Both the adenosine and inorganic phosphate are then incorporated into the liver ATP pools (steady state levels), effectively expanding-these pools (Rapaport and Zamecnik 1976; Rapaport and Fontaine 1989). The turnover of the expanded liver ATP pools, ATP pools which supply the adenosine precursor for red blood cell ATP synthesis, then lead to the expansion of red blood cell ATP pools. Expanded red blood cell ATP pools are in turn released from red blood cells into the blood plasma compartment (extracellular) via a non-hemolytic mechanism, where they are rapidly degraded to adenosine and inorganic phosphate (Slakey et al. 1990; Rapaport and Fontaine 1989; Rapaport 1990). The overall established mechanism thus provides for the slow, continuous release of adenosine in the blood plasma after the release of ATP at a preferred position along the distal part of the small intestine.

EXAMPLE 1

Therapeutic compositions consisting of 250 milligrams and 500 milligrams ATP tablets were formulated.

| Formulation Material | 250 mg ATP Tablet | 500 mg ATP Tablet |
|---|---|---|
| Adenosine 5'-triphosphate (Disodium salt) | 250 mg | 500 mg |
| Microcrystalline Cellulose | 200 mg | 200 mg |
| Maltodestrin | 200 mg | 100 mg |
| Magnesium Stearate | 10 mg | 20 mg |
| Sylox Silica ($SiO_2$) | 10 mg | 20 mg |
| Total | 670 mg | 825 mg |

ATP tablets formulation materials were compressed into tablets utilizing an oval punch. The tablets were without prominent edges and exhibited smooth concave surfaces. The tablets exhibited excellent mechanical strength and proved to be suitable for enteric coating. Six volunteer subjects ingested 1000 mg per day of the 250 mg or 500 mg ATP tablets, for a period of one month. No noticeable side effects were reported.

EXAMPLE 2

Each of the ATP-formulation tablets was coated with four different types of coating. The primary considerations in selecting these coating materials were that they should be of sufficient mechanical strength, provide good protection in acidic media and release the therapeutic composition of ATP at pH 6.8 or higher. The following enteric formulations were used:
1. Eudragit FS30D, which is an acqueous version of Eudragit S, coated to 8% coating.
2. Eudragit S 100, coated from acetone/methanol to a 6% coating.
3. Eudragit S 100, coated from acetone/methanol to a 8% coating. All of the above coatings release ATP at a pH of 7.0–7.2.
4. A mixture of Eudragit L100 (dissolves at pH 5.5) and Eudragit S100 (at a 20:80 ratio) coated from acetone/methanol to a 8% coating. Enteric coating number 4 released ATP at a pH of 6.7–6.8.

All four enteric coating formulations were stable and completely resisted simulated gastric fluid (no enzymes) test for over 2 hours. Six human volunteers ingested a total of 1000 milligrams of each of the four types of enteric coated ATP pills per day (two 500 mg pills per day, one in the morning and one in the evening) for a period of two weeks per type of enteric coating. No side effects or discomfort of any type were reported. The ATP pills were completely safe over the short term.

EXAMPLE 3

Two overweight human volunteers ingested 1000 mg per day of enteric coated ATP pills of enteric coating type 4 of Example 2. The subjects were not coffee drinkers or consumers of any other form of caffeine. After three weeks, one subject lost 4 pounds and the other subject lost 6 pounds without altering any other behavioral parameter such as diet or exercise.

EXAMPLE 4

Two overweight human volunteers who are coffee drinkers, consuming an average of two cups of coffee per day, or 110–150 milligrams of caffeine, ingested 1000 mg per day of enteric coated ATP pills of enteric coating type 4 of Example 2. After three weeks one subject lost 5 pounds and the other subject lost 6 pounds without altering any other behavioral parameter such as diet or exercise.

The data discussed above lead to the following conclusions:

A safe, stable, ingestable therapeutic composition of adenosine 5'-triphosphate disodium (ATP) in a form of a tablet containing more than 100 milligrams of ATP can be prepared using binders, fillers and stabilizers well-known to the skilled artisan.

A safe, stable ingestable therapeutic composition of ATP in a form of an enteric coated pill designed to dissolve in the distal part of the small intestine, can be prepared containing more than 100 milligrams of ATP per pill. The distal portion of the small intestine, the ileum, contains the lowest levels of catabolic enzymes catalyzing the degradation of ATP and adenosine.

A method for the chronic continuous administration of adenosine, which is the major catabolic product of its pro-drug ATP, has been unexpectedly produced utilizing the oral therapeutic compositions outlined in 1 and 2 above. Contrary to methods of the present invention, administration of adenosine or any of its pro-drugs by injection or infusion results in the acutely elevated levels of adenosine.

A method for the desensitization of adenosine receptors in a human by exposing adenosine receptors to chronically elevated levels of their natural agonist, adenosine.

A method for achieving weight loss in an overweight or obese human by desensitization of adipose tissue $A_1$ adenosine receptors. The interaction of endogenous adenosine with the $A_1$ adenosine receptors of adipose tissue is known to the skilled artisan to inhibit lipolysis or the degradation of fat. The unexpected finding is of a method for exposing these receptors to chronically elevated levels of adenosine, which desensitize these receptors towards the action of adenosine, endogenous or exogenous, resulting in the stimulation of lipolysis in humans. The reason being that once the receptors are desensitized, their density (numbers) as well as their activities are significantly diminished, abolishing the effects of adenosine in the inhibition of lipolysis.

A method for achieving weight loss in an overweight or obese human by utilizing methods described above coupled with the consumption of average levels of caffeine. Caffeine is a known antagonist of adenosine for the $A_1$ adenosine receptors of adipose tissue. Exposure of the desensitized receptors to caffeine during or after the chronic administration of adenosine, results in further stimulation of lipolysis and weight loss in humans. Once the adipose tissue $A_1$ adenosine receptors are desensitized towards adenosine, their sensitivity towards caffeine, an adenosine antagonist, is increased yielding additional inhibition of the activities of endogenous or exogenous adenosine at these receptors.

References Cited

Arciero P. J. et al.: Effects of caffeine ingestion on kinetics, fat oxidation, and energy expenditure in younger and older men. Am. J. Physiol. 268: E1192–E1198, 1995.

Burnstock G.: Purinergic Mechanisms. in Ann. N.Y. Acad. Sci. vol. 603, Biological Actions of Extracellular ATP. 1990, pp 1–17.

Council on Scientific Affairs, J. Amer. Med. Assoc.: Treatment of obesity in adults. JAMA 260: 2547–2551, 1988.

Hoppe E. and Lohse M. J.: Desensitization of $A_1$ adenosine receptors. in Adenosine and Adenine Nucleotides: from Molecular Biology to Integrative Physiology, Belardinelli L. and Pelleg A. Editors, Kluwer Publishers, 1995, pp 133–138.

Jacobson K. A. and van Rhee A. M.: Development of selective purinoceptor agonists and antagonists. in Purinergic Approaches in Experimental Therapeutics, Jacobson K. A. and Jarvis M. F., Editors, Wiley-Liss, 1997, pp 101–128.

Kollias-Baker C. et al.: Myocardial adenosine receptors. in Adenosine and Adenine Nucleotides: from Molecular Biology to Integrative Physiology, Belardinelli L. and Pelleg A., Editors, Kluwer Publishers, 1995, pp 221–229.

LaNoue K. F. and Martin L. F.: Abnormal At adenosine receptor function in genetic obesity. FASEB. J. 8: 72–80, 1994.

Lee H. T. et al.: Cardiac desensitization to adenosine analogues after prolonged R-PIA infusion in vivo. Am. J. Physiol. 265: H1916–H1927, 1993.

Linden J.: Structure and function of $A_1$ adenosine receptors. FASEB J. 5: 2668–2676, 1991.

Linden J.: Allosteric enhancement of adenosine receptors in Purinergic Approaches in Experimental Therapeutics, Jacobson K. A. and Jarvis M. F. Editors, Wiley-Liss, 1997, pp 85–97.

Mohamedali K. A. et al.: The highest levels of purine catabolic enzymes in mice are present in the proximal small intestine. J. Biol. Chem. 268: 23728–23733, 1993.

Rapaport E. and Zamecnik P. C.: Incorporation of adenosine into ATP: formation of compartmentalized ATP. Proc. Natl. Acad. Sci. USA 73: 3122–3125, 1976.

Rapaport E. and Fontaine J.: Generation of extracellular ATP in blood and its mediated inhibition of host weight loss in tumor-bearing mice. Biochem. Pharmacol. 38: 4261–4266, 1989.

Rapaport E. and Fontaine J.: Anticancer activities of adenine nucleotides in mice are mediated through expansion of erythrocyte ATP pools. Proc. Natl. Acad. Sci. USA 86: 1662–1666, 1989.

Rapaport E.: Mechanisms of anticancer activities of adenine nucleotides in tumor-bearing hosts. in Ann. N.Y. Acad. Sci., vol. 603, Biological Actions of Extracellular ATP, 1990, pp 142–150.

Shryock J. et al.: Down regulation and desensitization of $A_1$-adenosine receptors in embryonic chicken heart. Am. J. Physiol. 256: H321–H327, 1989.

Slakey L. L. et al.: A comparison of ectonucleotidase activities on vascular endothelial and smooth muscle cells. in Ann. N.Y. Acad. Sci., vol. 603, Biological Actions of Extracellular ATP, 1990, pp 366–378.

Van der Graaf P. H. et al.: Mechanism-based pharmacokinetic-pharmacodynamic modeling of antilipolytic effects of adenosine $A_1$ receptor agonists in rats: prediction of tissue-dependent efficacy in vivo. J. Pharmacol. Exp. Ther. 290: 702–709, 1999.

Van Schaick E. A. et al.: Metabolic and cardiovascular effects of the adenosine $A_1$ receptor agonist $N^6$-(p-sulphenyl)adenosine in diabetic Zucker rats: influence of the disease on the selectivity of action. J. Pharmacol. Exp. Ther. 287: 21–30, 1998.

Williams M. and Burnstock G.: Purinergic neurotransmission and neuromodulation: A historical perspective. in Purinergic Approaches in Experimental Therapeutics, Jacobson K. A. and Jarvis M. F. Editors, Wiley-Liss, 1997, pp 3–26.

Xu B. et al.: $A_1$ adenosine receptor antagonism improves glucose tolerance in Zucker rats. Am. J. Physiol. 274: E271–E279, 1998.

| U.S. Patent Documents | | | |
|---|---|---|---|
| 5,422,352 | June, 1995 | Astrup | 514/264 |
| 5,480,657 | January, 1996 | Allen | 424/617 |
| 5,679,358 | October, 1997 | Bombardelli et al | 424/401 |
| 5,798,101 | August, 1998 | Haveson | 424/195.1 |

Having thus described my invention, what I claim as new and useful and desire to secure by letters patent is:

1. A method for treating overweight and/or obesity which comprises administering to a human suffering from overweight and/or obesity an effective amount of at least one member selected from the group consisting of: (a) a mixture of adenosine and inorganic phosphate; and/or (b) an adenine nucleotide wherein said adenine nucleotide contains adenosine moiety(ies) and phosphate moiety(ies) and undergoes rapid degradation to adenosine and inorganic phosphate.

2. The method of claim 1 wherein the adenine nucleotide and/or adenosine and inorganic phosphate are administered to an overweight and/or obese human in order to initiate weight loss.

3. The method of claim 1 wherein the adenine nucleotide and/or adenosine and inorganic phosphate arc administered to an overweight and/or obese human in order to prevent additional weight gain.

4. The method of claim 1 wherein adenosine 5'-monopliosphate is administered to said human.

5. The method of claim 1 wherein adenosine and inorganic phosphate are administered to said human.

6. The method of claim 1 wherein the amount of adenosine or adenine nucleotide is about 0.1–100 milligrams/kg of body weight per 24 hours and said administering is oral or sublingual.

7. The method of claim 1 wherein the amount of adenosine or adenine nucleotide is 0.1–100 milligrams/kg of body weight per 24 hours and said administering is topical.

8. The method of claim 1 wherein the amount of adenosine or adenine nucleotide is 0.01–10 milligrams/kg of body weight per 24 hours and said administering is by injection.

9. The method of claim 1 wherein the amount of adenosine or adenine nucleotide is 0.001–1 milligrams/kg of body weight per 24 hours and said administering is by infusion.

10. The method of claim 1 wherein adenine nucleotides are administered to said human suffering from overweight and/or obesity as pharmaceutically acceptable salts thereof, chelates thereof, metal complexes thereof or liposomes thereof.

11. The method of claim 1 wherein adenosine 5'-triphosphate is administered to said human.

12. The method of claim 11 wherein the amount of adenosine 5'-triphosphate is about 0.1–100 milligrams/kg of body weight per 24 hours and said administering is oral or sublingual.

13. The method of claim 11 wherein the amount of adenosine 5'-triphosphate is about 0.1–100 milligrams/kg of body weight per24 hours and said administering is topical.

14. The method of claim 11 wherein the amount of adenosine 5'-triphosphate is about 0.01–10 milligrams/kg of body weight per 24 hours and said administering is by injection.

15. The method of claim 11 wherein the amount of adenosine 5'-triphosphate is about 0.001–1 milligrams/kg of body weight per 24 hours and said administering is by infusion.

16. The method of claim 1 wherein said treating of said human suffering from overweight and/or obesity is continuous.

17. The method of claim 16 wherein said treating of said human suffering from overweight and/or obesity is over a period of at least a week.

18. The method of claim 16 wherein said treating of said human suffering from overweight and/or obesity is over a period of at least a month.

19. The method of claim 16 wherein said treating of said human suffering from overweight and/or obesity is over a period of at least a year.

20. A process for treating overweight and/or obesity which comprises administering to a human suffering from overweight and/or obesity an effective amount of at least one member selected from the group consisting of: (a) a mixture of adenosine and inorganic phosphate; and/or (b) an adenine nucleotide wherein said adenine nucleotide contains adenosine moiety(ies) and phosphate moiety(ies) and undergoes rapid degradation to adenosine and inorganic phosphate, whereby adenosine desensitizes adenosine receptors in said human.

21. The process of claim 20 wherein said treating comprises at least one compound selected from the group of adenosine and inorganic phosphate, adenosine 5'-monophosphate, adenosine 5'-triphosphate, pharmaceutically acceptable salts thereof, chelates thereof, metal complexes thereof or liposomes thereof.

22. The process of claim 20 wherein said treating comprises adenosine 5'-monophosphate.

23. The process of claim 20 wherein said treating comprises adenosine 5'-triphosphate.

24. The process of claim 23 wherein amount of adenosine 5'-triphosphate is about 0.1–100 milligrams/kg of body weight per 24 hours and said treating is oral or sublingual.

25. The process of claim 23 wherein amount of adenosine 5'-triphosphate is about 0.1–100 milligrams/kg of body weight per 24 hours and said treating is topical.

26. The process of claim 23 wherein amount of adenosine 5'-triphosphate is about 0.01–10 milligrams/kg of body weight per 24 hours and said treating is by injection.

27. The process of claim 23 wherein amount of adenosine 5'-triphosphate is about 0.001–1 milligrams/kg of body weight per 24 hours and said treating is by infusion.

* * * * *

UNITED STATES PATENT AND TRADEMARK OFFICE
CERTIFICATE OF CORRECTION

PATENT NO.        : 6,723,737 B1
APPLICATION NO. : 10/111167
DATED             : April 20, 2004
INVENTOR(S)       : Eliezer Rapaport It is certified that error appears in the above-identified patent and that said Letters Patent is hereby corrected as shown below:

In the Claims

Claim 3:   please amend claim 3 to read "The method of claim 1 wherein the adenine nucleotide and/or adenosine and inorgnic phosphate are"

Claim 4:   please amend claim 4 to read "adenosine 5'-monophosphate"

Signed and Sealed this

Twenty-ninth Day of August, 2006

JON W. DUDAS
*Director of the United States Patent and Trademark Office*